United States Patent
Schultz et al.

(10) Patent No.: US 11,471,284 B2
(45) Date of Patent: Oct. 18, 2022

(54) SPINAL IMPLANT SYSTEM

(71) Applicant: Stryker European Operations Holdings LLC, Kalamazoo, MI (US)

(72) Inventors: Christian Karl Schultz, Hoboken, NJ (US); Jason H. Steinke, Hoboken, NJ (US); Steven Willis, Midland Park, NJ (US); Justyna Zielinska, Linden, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 41 days.

(21) Appl. No.: 17/158,599

(22) Filed: Jan. 26, 2021

(65) Prior Publication Data
US 2021/0145590 A1 May 20, 2021

Related U.S. Application Data

(62) Division of application No. 15/938,139, filed on Mar. 28, 2018, now Pat. No. 10,966,835.
(Continued)

(51) Int. Cl.
*A61F 2/30* (2006.01)
*A61F 2/44* (2006.01)
*A61B 17/80* (2006.01)

(52) U.S. Cl.
CPC .......... *A61F 2/30749* (2013.01); *A61F 2/442* (2013.01); *A61F 2/447* (2013.01); *A61F 2/4455* (2013.01); *A61F 2/4465* (2013.01); *A61B 17/8042* (2013.01); *A61F 2002/305* (2013.01); *A61F 2002/3008* (2013.01); *A61F 2002/30113* (2013.01); *A61F 2002/30125* (2013.01); *A61F 2002/30136* (2013.01); *A61F 2002/30153* (2013.01); *A61F 2002/30154* (2013.01); *A61F 2002/30187* (2013.01); *A61F 2002/30387* (2013.01); *A61F 2002/30469* (2013.01); *A61F 2002/30481* (2013.01); *A61F 2002/30517* (2013.01); *A61F 2002/30594* (2013.01); *A61F 2002/30604* (2013.01);
(Continued)

(58) Field of Classification Search
None
See application file for complete search history.

(56) References Cited

U.S. PATENT DOCUMENTS

| | | | |
|---|---|---|---|
| 3,641,590 A | 2/1972 | Michele | |
| 4,743,262 A | 5/1988 | Tronzo | |

(Continued)

FOREIGN PATENT DOCUMENTS

| | | |
|---|---|---|
| EP | 1520545 A1 | 4/2005 |
| WO | 2008124355 A1 | 10/2008 |

OTHER PUBLICATIONS

Extended European Search Report for Application No. 18164405.5 dated Aug. 17, 2018, 9 pages.

*Primary Examiner* — Tessa M Matthews
(74) *Attorney, Agent, or Firm* — Duane Morris LLP

(57) ABSTRACT

A prosthesis for spinal surgery includes a spacer adapted to be secured into the bone and attached to one of a plurality of configuration plates. The configuration plates are interchangeable and each one is configured to utilize a different combination of bone screws, anchors or both. The prosthesis may further include a retaining mechanism to prevent bone screws and/or anchors from backing out.

19 Claims, 19 Drawing Sheets

Related U.S. Application Data

(60) Provisional application No. 62/478,162, filed on Mar. 29, 2017.

(52) U.S. Cl.
CPC .............. *A61F 2002/30782* (2013.01); *A61F 2002/30784* (2013.01); *A61F 2002/30787* (2013.01); *A61F 2002/30841* (2013.01); *A61F 2002/30845* (2013.01); *A61F 2002/30879* (2013.01); *A61F 2002/30883* (2013.01); *A61F 2002/30884* (2013.01); *A61F 2002/30904* (2013.01)

(56) References Cited

U.S. PATENT DOCUMENTS

| | | |
|---|---|---|
| 5,314,477 A | 5/1994 | Marnay |
| 5,609,635 A | 3/1997 | Michelson |
| 5,683,394 A | 11/1997 | Rinner |
| 5,709,683 A | 1/1998 | Bagby |
| 5,713,899 A | 2/1998 | Marnay et al. |
| 5,893,889 A | 4/1999 | Harrington |
| 6,096,080 A | 8/2000 | Nicholson et al. |
| 6,113,638 A | 9/2000 | Williams et al. |
| 6,206,882 B1 | 3/2001 | Cohen |
| 6,235,059 B1 | 5/2001 | Benezech et al. |
| 6,447,546 B1 | 9/2002 | Bramlet et al. |
| 6,629,998 B1 | 10/2003 | Lin |
| 6,743,256 B2 | 6/2004 | Mason |
| 7,048,766 B2 | 5/2006 | Ferree |
| 7,060,097 B2 | 6/2006 | Fraser et al. |
| 7,232,464 B2 | 6/2007 | Mathieu et al. |
| 7,238,203 B2 | 7/2007 | Bagga et al. |
| 7,331,995 B2 | 2/2008 | Eisermann et al. |
| 7,594,931 B2 | 9/2009 | Louis et al. |
| 7,658,766 B2 | 2/2010 | Melkent et al. |
| 7,695,516 B2 | 4/2010 | Zeegers |
| 7,749,271 B2 | 7/2010 | Fischer et al. |
| 7,846,207 B2 | 12/2010 | Lechmann et al. |
| 8,349,015 B2 | 1/2013 | Bae et al. |
| 8,747,412 B2 | 6/2014 | Bae et al. |
| 9,033,993 B2 | 5/2015 | Bae et al. |
| 9,480,577 B2 | 11/2016 | Despiau et al. |
| 9,700,434 B2 | 7/2017 | Bae et al. |
| 2002/0004683 A1 | 1/2002 | Michelson |
| 2002/0165613 A1 | 11/2002 | Lin et al. |
| 2003/0195632 A1 | 10/2003 | Foley et al. |
| 2004/0148028 A1 | 7/2004 | Ferree et al. |
| 2005/0149193 A1 | 7/2005 | Zucherman et al. |
| 2006/0085071 A1 | 4/2006 | Lechmann et al. |
| 2008/0249575 A1 | 10/2008 | Waugh et al. |
| 2008/0287999 A1 | 11/2008 | Markworth |
| 2009/0005870 A1 | 1/2009 | Hawkins et al. |
| 2009/0088849 A1 | 4/2009 | Armstrong et al. |
| 2009/0164020 A1 | 6/2009 | Janowski et al. |
| 2009/0224023 A1 | 9/2009 | Moskowitz et al. |
| 2009/0240333 A1 | 9/2009 | Trudeau et al. |
| 2010/0004747 A1 | 1/2010 | Lin |
| 2010/0185292 A1 | 7/2010 | Hochschuler et al. |
| 2010/0204737 A1 | 8/2010 | Bae et al. |
| 2010/0268279 A1 | 10/2010 | Gabelberger et al. |
| 2010/0286777 A1 | 11/2010 | Errico et al. |
| 2011/0029023 A1 | 2/2011 | Tornier |
| 2011/0160866 A1 | 6/2011 | Laurence et al. |
| 2011/0230971 A1* | 9/2011 | Donner .................. A61F 2/442 606/246 |
| 2011/0301713 A1 | 12/2011 | Theofilos |
| 2011/0319893 A1 | 12/2011 | Stanaford et al. |
| 2012/0078373 A1 | 3/2012 | Gamache et al. |
| 2012/0215315 A1 | 8/2012 | Hochschuler et al. |
| 2012/0215316 A1 | 8/2012 | Mohr et al. |
| 2012/0232595 A1 | 9/2012 | Holschlag |
| 2012/0253406 A1 | 10/2012 | Bae et al. |
| 2012/0277870 A1 | 11/2012 | Wolters et al. |
| 2012/0289978 A1 | 11/2012 | Jacob |
| 2013/0123925 A1 | 5/2013 | Patterson et al. |
| 2014/0052258 A1* | 2/2014 | Ball .................. A61B 17/8047 623/17.16 |
| 2014/0074241 A1* | 3/2014 | McConnell ............. A61F 2/447 623/17.16 |
| 2014/0088711 A1 | 3/2014 | Chin et al. |
| 2014/0277491 A1 | 9/2014 | Fang et al. |
| 2015/0018956 A1 | 1/2015 | Steinmann et al. |
| 2015/0057754 A1 | 2/2015 | Reed et al. |
| 2015/0328010 A1 | 11/2015 | Martynova et al. |
| 2016/0113781 A1 | 4/2016 | Laurence et al. |
| 2016/0367379 A1 | 12/2016 | Refai |
| 2019/0053907 A1 | 2/2019 | Gregersen et al. |
| 2021/0322185 A1* | 10/2021 | Reed .................... A61F 2/4465 |

\* cited by examiner

SPINAL IMPLANT SYSTEM

CROSS-REFERENCE TO RELATED APPLICATIONS

The present application is a divisional of U.S. application Ser. No. 15/938,139, filed Mar. 28, 2018, which claims the benefit of the filing date of U.S. Provisional Patent Application No. 62/478,162 filed Mar. 29, 2017, the disclosure of which is hereby incorporated herein by reference.

BACKGROUND OF THE INVENTION

The present invention relates, in general, to an intervertebral system allowing a surgeon to choose the method of fixation of a spacer at the time of surgery.

Back pain can be caused by any one of several problems that affect intervertebral discs of the spine, including, for example, degeneration, bulging, herniation, thinning of a disc, or abnormal movement. Generally, the pain is attributable to friction or pressure that inevitably occurs when one or both adjacent vertebras exert uneven pressure on the disc.

In response to such problems, a typical remedy is to perform spinal fusion, including for example, interbody, intervertebral, cervical, thoracic, or lumbar fusion surgery (all generically referred to herein as "IF"), which fuse together the two vertebrae adjacent the defective disc to form a single, solid bone. Presently, in an IF procedure, the problematic disc is removed and a spacer is implanted into the space. The spacer generally engages adjacent vertebral bodies to fuse and immobilize the site and mitigate patient discomfort.

There are a variety of fixation methods used to retain the spacer in its position. For example, screws can be inserted into holes in the spacer to engage the bone to secure the spacer thereto. Frequently, a screw back-out mechanism is used to prevent such screws from coming loose from the spacer, causing the spacer to become dislodged or unstable in the body. Alternatively, or in addition to the use of screws, a spacer may have anchors coupled thereto that extend into the bone to fix the spacer in position. Whether screws and/or anchors are used may depend on the surgeon's preference, the patient's anatomy, and the pathology. Existing systems dedicate the surgeon to one method of fixation and often one way to anchor it to the adjacent vertebrae.

There is a need in the art for an implant system that allows more autonomy to a surgeon to choose the method of fixation during surgery.

BRIEF SUMMARY OF THE INVENTION

A first aspect of the invention is a spacer for intervertebral disc repair including a hole for receiving a screw and a channel for receiving an anchor.

In accordance with certain embodiments of this first aspect, a perimeter of the hole at a location about a central axis of the hole may be fully enclosed within the spacer. The central axis of the hole may extend through a superior surface and a front surface of the spacer. The central axis of the hole may extend through an inferior surface and a front surface of the spacer. The spacer may further include a second hole having a perimeter at a location about a central axis of the second hole that is fully enclosed within the spacer. The central axis of the second hole may extend through an inferior surface and a front surface of the spacer. The central axis of the second hole may extend through a superior surface and a front surface of the spacer. The spacer may further include a third hole having a perimeter at a location about a central axis of the third hole that is fully enclosed within the spacer. The central axis of the third hole may extend through a superior surface and a front surface of the spacer.

The channel may be a dovetail slot and may extend along a superior surface or an inferior surface of the spacer. The channel may be open toward the superior or inferior surface along which it extends. The channel may extend between and intersect both a leading side and a trailing side of the spacer. The channel may extend along a central axis that forms a non-perpendicular angle with the leading side of the spacer. A perimeter of the channel about a central axis of the channel may not be fully enclosed within the spacer at any location about the central axis of the channel. The spacer may further include a second channel that is a dovetail slot extending along the same one of the superior and inferior surfaces. The spacer may further include a second channel that is a dovetail slot extending along the other one of the superior and inferior surfaces.

A second aspect of the invention is a kit for intervertebral disc repair including a spacer for intervertebral disc repair including a hole for receiving a screw and a channel for receiving an anchor, a first plate configured to attach to the spacer, the first plate having a hole extension that aligns with the hole when the first plate is attached to the spacer, and a second plate configured to attach to the spacer, the second plate having a channel extension that aligns with the channel when the second plate is attached to the spacer.

In accordance with certain embodiments of this second aspect, any of the aforementioned configurations of the spacer can be included in the kit. The kit may further include an anchor configured to extend into the channel and the channel extension and into one of the adjacent vertebrae when the second plate is attached to the spacer. The anchor may include an interconnection portion to slidingly engage the spacer, a fixation portion spaced apart from the interconnection portion to fix the anchor to an adjacent vertebra, and a leg connecting the fixation portion to the interconnection portion. The kit may further include a screw configured to extend through the hole and the hole extension and into one of the adjacent vertebrae when the first plate is attached to the spacer. The channel of the spacer may include four channels and the channel of the second plate may include four channels configured to align with the four channels of the spacer when the second plate is attached to the spacer. The kit may further include a securing plate configured to attach to the first plate. The securing plate may include a slot therein. The slot may be configured to align with the hole of the first plate when the securing plate is attached to the first plate.

The kit may further include a third plate configured to attach to the spacer, the third plate having a hole extension that aligns with the hole when the third plate is attached to the spacer and a channel extension that aligns with the channel when the third plate is attached to the spacer. The hole of the spacer may include two holes and the channel of the spacer may include two channels, and the hole of third plate may include two holes and the channel of the third plate may include two channels, the holes and channels of the third plate configured to align with the holes and channels of the spacer, respectively, when the third plate is attached to the spacer. The kit may further include a securing plate configured to attach interchangeably with the first and third plates. The securing plate may include a slot therein. The slot may be configured to align with the hole of the first plate or the hole of the third plate when the securing plate is attached to the first or third plate.

A third aspect of the invention is a kit for intervertebral disc repair including a spacer for intervertebral disc repair including a hole for receiving a screw and a channel for receiving an anchor, and a securing plate configured to engage the spacer, wherein a portion of the securing plate overlies the hole and the channel when the securing plate is engaged to the spacer to block a screw from backing out of the hole and to block an anchor from backing out of the channel.

In accordance with certain embodiments of this third aspect, any of the aforementioned configurations of the spacer can be included in the kit. The securing plate may further include a slot configured to allow the retaining mechanism to compress. The kit may further include an anchor configured to extend into the channel and the channel extension and into one of the adjacent vertebrae when the second plate is attached to the spacer. The anchor may include an interconnection portion to slidingly engage the spacer, a fixation portion spaced apart from the interconnection portion to fix the anchor to an adjacent vertebra, and a leg connecting the fixation portion to the interconnection portion. The kit may further include a screw configured to extend through the hole of the spacer and into one of the adjacent vertebrae.

A fourth aspect of the invention is a method of using of a kit for intervertebral disc repair, the kit including a spacer for intervertebral disc repair including a hole for receiving a screw and a channel for receiving an anchor, a first plate configured to attach to the spacer, the first plate having a hole extension that aligns with the hole when the first plate is attached to the spacer, and a second plate configured to attach to the spacer, the second plate having a channel extension that aligns with the channel when the second plate is attached to the spacer, with the method including the steps of attaching one of the first or second plates to the spacer, inserting the spacer-plate configuration into the disc space, and inserting a screw into the hole and the hole extension of the first plate and into communication with an adjacent vertebra or inserting an anchor into the channel and the channel extension of the second plate and into communication with an adjacent vertebra.

In accordance with certain embodiments of this fourth aspect, any of the aforementioned configurations of the kit can be utilized by the method. The method may further include the step of evaluating bone integrity of vertebrae adjacent the disc space. The method may further include the step of selecting the first plate or the second plate to be used with the spacer. The inserting step may be carried out in an anterior approach. The inserting step may be carried out in a lateral approach.

A fifth aspect of the invention is a method of using a kit for intervertebral disc repair, the kit including a spacer for intervertebral disc repair including a hole for receiving a screw and a channel for receiving an anchor, a first plate configured to attach to the spacer, the first plate having a hole extension that aligns with the hole when the first plate is attached to the spacer, a second plate configured to attach to the spacer, the second plate having a channel extension that aligns with the channel when the second plate is attached to the spacer, and a third plate configured to attach to the spacer, the third plate having a hole extension that aligns with the hole when the third plate is attached to the spacer and a channel extension that aligns with the channel when the third plate is attached to the spacer, with the method including the steps of attaching one of the first, second, or third plates to the spacer, inserting the spacer-plate configuration into the disc space, and inserting a screw into the hole and the hole extension of the first plate and into communication with an adjacent vertebra, inserting an anchor into the channel and the channel extension of the second plate and into communication with an adjacent vertebra, or inserting a screw into the hole and the hole extension of the third plate and into communication with an adjacent vertebra and inserting an anchor into the channel and the channel extension of the third plate and into communication with an adjacent vertebra.

In accordance with certain embodiments of this fifth aspect, any of the aforementioned configurations of the kit can be utilized by the method. The method may further include the step of evaluating bone integrity of vertebrae adjacent the disc space. The method may further include the step of selecting the first plate, the second plate, or the third plate to be used with the spacer.

A sixth aspect of the invention is a method of using a kit for intervertebral disc repair, the kit including a spacer for intervertebral disc repair including a hole for receiving a screw and a channel for receiving an anchor, a first plate configured to attach to the spacer, the first plate having a hole extension that aligns with the hole when the first plate is attached to the spacer, a second plate configured to attach to the spacer, the second plate having a channel extension that aligns with the channel when the second plate is attached to the spacer, a third plate configured to attach to the spacer, the third plate having a hole extension that aligns with the hole when the third plate is attached to the spacer and a channel extension that aligns with the channel when the third plate is attached to the spacer, and a securing plate configured to attach interchangeably with any of the first, second, and third plates, with the method including the steps of attaching one of the first, second, or third plates to the spacer, inserting the spacer-plate configuration into the disc space, inserting a screw into the hole and the hole extension of the first plate and into communication with an adjacent vertebra, inserting an anchor into the channel and the channel extension of the second plate and into communication with an adjacent vertebra, or inserting a screw into the hole and the hole extension of the third plate and into communication with an adjacent vertebra and inserting an anchor into the channel and the channel extension of the third plate and into communication with an adjacent vertebra and when the first plate or the third plate is attached to the spacer, attaching the securing plate to the first plate or the third plate. In accordance with certain embodiments of this sixth aspect, any of the aforementioned configurations of the kit can be utilized by the method.

A seventh aspect of the invention is a method of using a kit for intervertebral disc repair, the kit including a spacer for intervertebral disc repair including a hole for receiving a screw and a channel for receiving an anchor, and a securing plate configured to engage the spacer, wherein a portion of the securing plate overlies the hole and the channel when the securing plate is engaged to the spacer to block a screw from backing out of the hole and to block an anchor from backing out of the channel, with the method including the steps of inserting the spacer into disc space, inserting a screw into the hole of the spacer, and attaching the securing plate to the spacer. In accordance with certain embodiments of this seventh aspect, any of the aforementioned configurations of the kit can be utilized by the method.

An eighth aspect of the invention is a method of using a kit for intervertebral disc repair, the kit including a spacer for intervertebral disc repair including a hole for receiving a screw and a channel for receiving an anchor, and a securing plate configured to engage the spacer, wherein a portion of the securing plate overlies the hole and the channel when the securing plate is engaged to the spacer to block a screw from backing out of the hole and to block an anchor from backing out of the channel, with the method including the steps of inserting the spacer into disc space, inserting an anchor into the channel of the spacer, and attaching the securing plate to the spacer. In accordance with certain embodiments of this eighth aspect, any of the aforementioned configurations of the kit can be utilized by the method.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which.

DETAILED DESCRIPTION

In describing certain aspects of the present invention(s), specific terminology will be used for the sake of clarity. However, the invention(s) is not intended to be limited to any specific terms used herein, and it is to be understood that each specific term includes all technical equivalents, which operate in a similar manner to accomplish a similar purpose.

Figure 1:
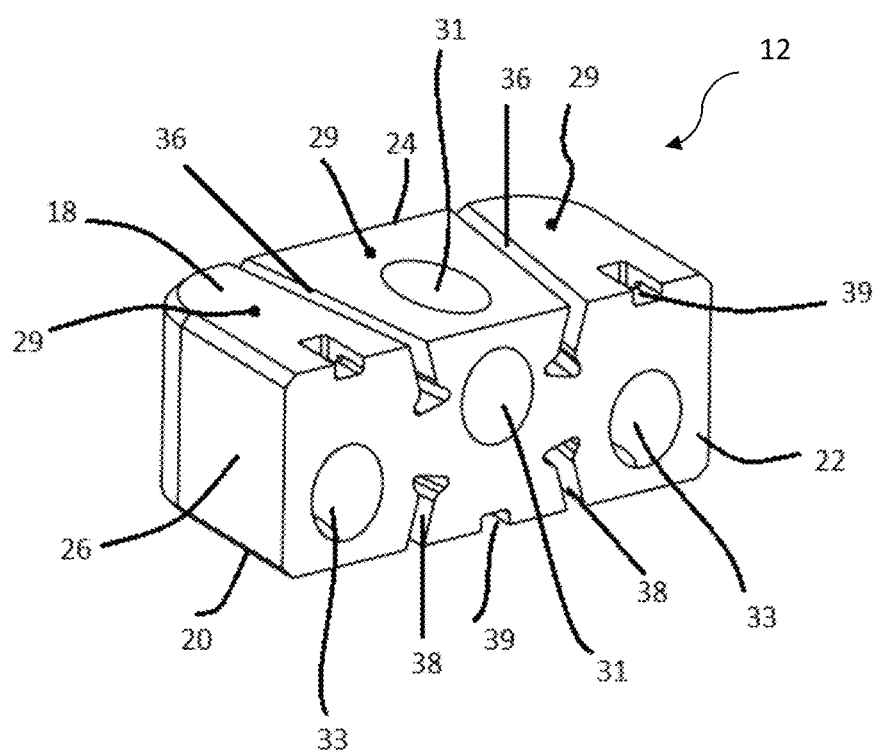
FIG. 1 is a perspective view of a spacer of a prosthesis, in accordance with one embodiment of the present invention.
Figure 2:
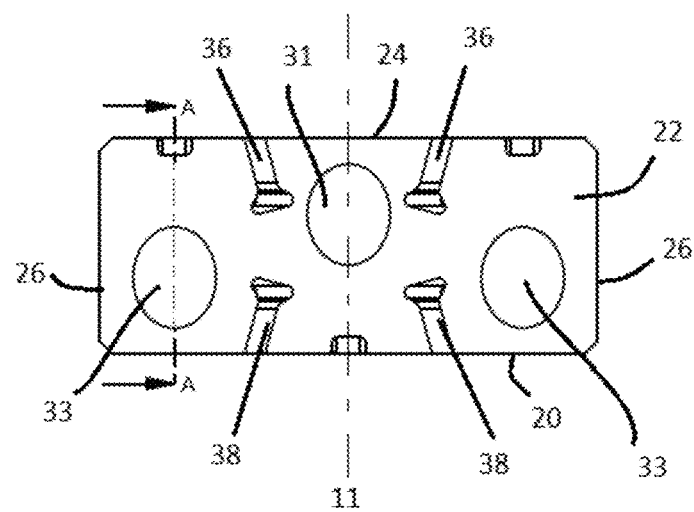
FIG. 2 is an anterior view of the spacer of FIG. 1.

Referring to FIGS. 1-2, an implant or spacer 12 according to one embodiment of the present invention includes top and bottom bone-contacting sides 18 and 20, respectively, a leading side 24, a trailing side 22 opposite the leading side 24, and two lateral sides 26 extending between the leading and trailing sides 22, 24. In the illustrated embodiment, the spacer 12 has a generally rectangular prismatic shape with posterior-facing edges extending between top and bottom sides 18, 20 being rounded. Alternatively, the spacer 12 may be a square, oval, circular, elliptical, or any other shape in the superior view. Top and bottom sides 18 and 20 may be flat, concave, convex, or any other shape in the anterior or lateral views. In particular, in a lateral view, the top and bottom sides 18, 20 may be curved or angled to give spacer 12 a lordotic shape.

Spacer 12 includes a hole 31 having at least a portion that is fully enclosed within the body of spacer 12. That is, hole 31 has a perimeter at at least one location about its central axis that is fully enclosed within the body of implant 12. The central axis of hole 31 extends through a superior surface and a front surface of the spacer, such that hole 31 extends at an angle from trailing side 22 to top side 18. As shown in FIGS. 1 and 2, hole 31 may be positioned generally centrally or between lateral sides 26 on trailing side 22 of spacer 12. Spacer 12 includes two additional holes 33 each also having a perimeter at at least one location about its central axis that is fully enclosed within the spacer. The central axes of holes 33 extend through an inferior surface and the front surface of the spacer, such that the holes 33 extend into spacer 12 at an angle from trailing side 22 to bottom side 20. Each hole 33 may be positioned between central line 11 and one of the lateral sides 26. In other embodiments, spacer 12 may have fewer or more holes positioned in the same or different locations and extending through spacer 12 at different angles to accommodate screws. In certain embodiments, the holes may only extend toward one of top and bottom sides 18, 20. In yet another embodiment, any or all of the holes may have a perimeter that is only partially enclosed within the spacer.

Spacer 12 has channels or tracks 36, 38 that extend across spacer 12 between and intersect with both leading side 24 and trailing side 22. As shown in FIGS. 1 and 2, channels 36, 38 are dovetail slots that are formed in spacer 12 in a truncated I-beam shape. However, in other examples, the channels 36, 38 may have a variety of shapes, including circular, rectangular, keyhole, T-shaped, etc. Each channel is preferably configured to have an enlarged profile away from the adjacent surface so that an anchor disposed therein can be secured from migrating out of that channel toward the surface. Each dovetail slot is configured to slideably engage with a mating feature on an anchor 80, described in detail below. Spacer 12 includes four channels, two channels 36 that are open toward top side 18 of spacer 12 and extend across top side 18 and two channels 38 that are open toward bottom side 20 of spacer 12 and extend across bottom side 20. As shown in FIGS. 1 and 2, each channel 36, 38 may extend along a central axis that is angled, i.e. forms a non-perpendicular angle, with respect to leading side 24 of spacer 12. Channels 36, 38 may extend across top and bottom sides 18, 20 at an angle with respect to leading side 24 so that, for example, two channels 36 are nearer each other on trailing side 22 than on leading side 24 such that they diverge. Further, each channel 36, 38 may have a perimeter about its central axis that is not fully enclosed within spacer 12 at any location along its central axis so that it is open in the superior or inferior direction, as the case may be.

Figure 2A:
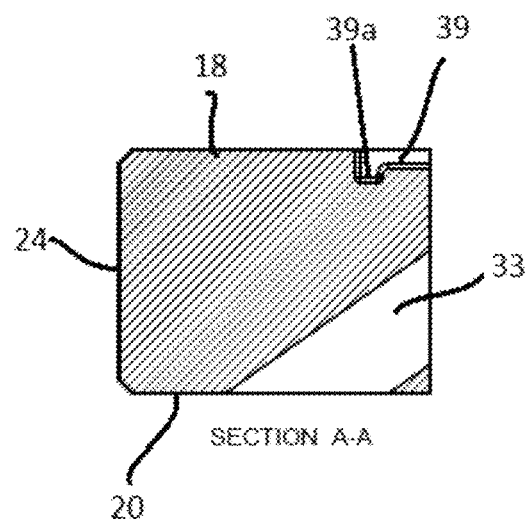
FIG. 2A is a cross section view along section A-A as shown in FIG. 2.

Spacer 12 includes a connection feature to allow for a mating connection with a corresponding feature on a cover plate 40, 140, 240. In the illustrated embodiment, the connection feature of spacer 12 is recesses 39, which are shaped and sized to couple with the corresponding connection feature of plates 40, 140, 240 (e.g. clips 55, 155, 255 described below). However, in other examples, the connection features of spacer 12 and the plates may include any feature known in the art to allow the two bodies to connect, such as for example compression technology. Other embodiments may also include recesses 39 and clips 55, 155, 255 in different quantities and/or in different locations, such as on lateral surfaces of the implant. As shown in FIGS. 1 and 2, two recesses 39 are disposed on top side 18 and one recess 39 is disposed on bottom side 20, each of which extend from leading side 24 toward trailing side 22. Each recess 39 is positioned generally adjacent to a hole 31, 33, though such positioning is not required. In other embodiments, spacer 12 may include more or fewer recesses 39 which may be disposed in a variety of positions on top and bottom sides 18 and 20 and/or lateral sides 26 to accommodate and secure a cover plate such as cover plate 40. As shown in FIG. 2A, recesses 39 are each shaped to include a groove 39a that extends into spacer 12 from the respective top or bottom side 18, 20 to allow for a mating feature of cover plate 40 to more securely attach cover plate 40 to spacer 12. In the present embodiment, both recesses 39 and grooves 39a are rectangular; however, in other examples, the recesses and grooves may take other shapes, including square, circle, oval, trapezoidal, etc.

Spacer 12 and/or the attached plate may further include teeth or serration on each of top and bottom sides 18, 20 to provide for fixation with adjacent vertebrae and may include openings to allow for receipt of bone in-growth material.

A prosthesis 10 according to one embodiment of the present invention includes a plate 40, 140, or 240 that attaches to spacer 12. Plates 40, 140, and 240 are interchangeable and are each connectable with spacer 12 to form a differently-configured prosthesis 10. Each plate 40, 140, 240 provides a different variation of fixation features, so that during surgery, a surgeon can choose which plate is most appropriate to use for a particular patient and/or objective. Plates 40, 140, 240 can include one or more of screw holes, dovetail slots, or both, so that bone screws, anchors, or both may be inserted into prosthesis 10, respectively. After selecting one of the plates, the surgeon can then attach it to spacer 12.

Plates 40, 140, and 240 share several common features, which are described first. Although reference numerals correspond to configuration plate 40, similar features included in plates 140 and 240 are represented with like numerals.

As shown in FIGS. 3-6, plate 40 includes a top side 42, a bottom side 44 opposite the top side, opposing lateral sides 46 extending between the top side 42 and the bottom side 44, a trailing side 48, and a leading side 50 opposite the trailing side.

Figure 4A:
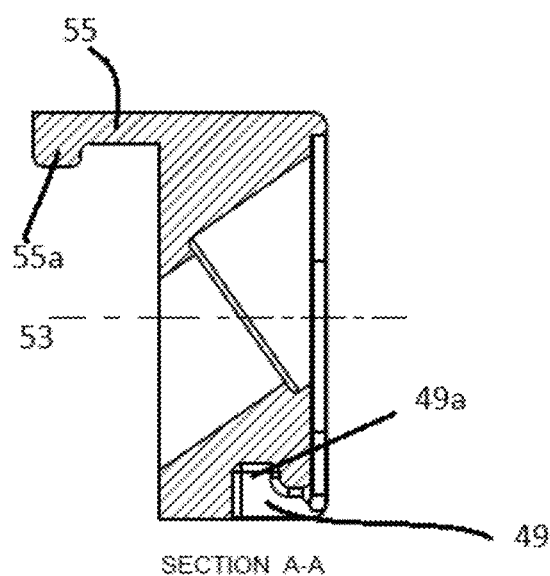
FIG. 4A is a cross section view along section A-A as shown in FIG. 4.
Figure 5:
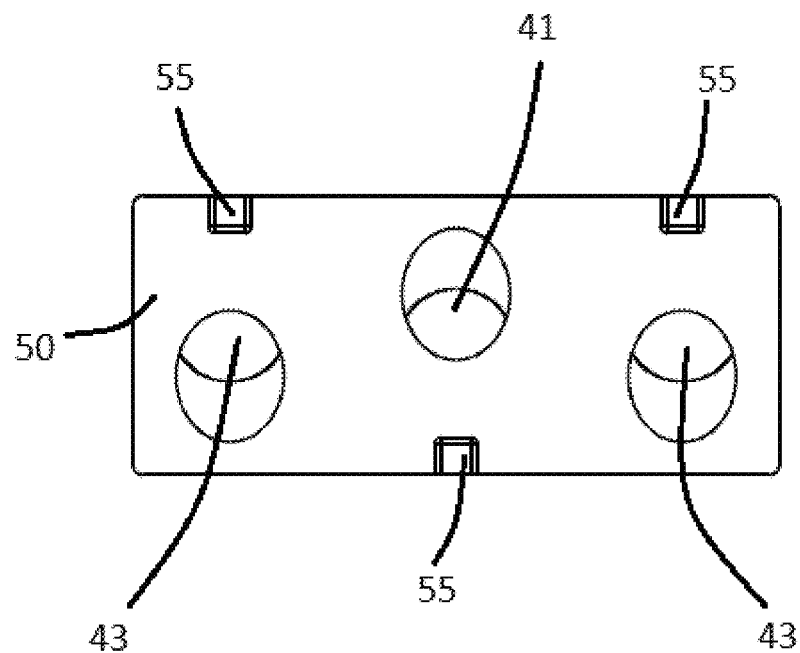
FIG. 5 is a posterior view of the configuration plate of FIG. 3.
Figure 6:
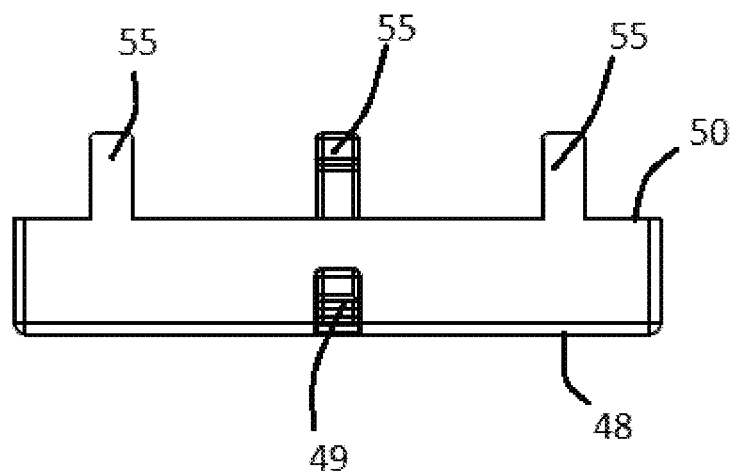
FIG. 6 is a superior view of the configuration plate of FIG. 3.

Plate 40 includes a connection feature to connect the plate to spacer 12. In the illustrated embodiment, the connection feature of plate 40 is clips 55. However, as described above with respect to recesses 39, clips 55 may be any corresponding feature that allows for connection of spacer 12 and plate 40. Additionally, the connection feature may be one such that only one common connection feature is required between spacer 12 and plate 40. In the illustrated embodiment, clips 55 each extend posteriorly away from leading side 50. As shown in FIGS. 5 and 6, plate 40 includes two clips 55 positioned generally superiorly of holes 43 and one clip 55 positioned generally inferiorly of hole 41. Clips 55 are sized and shaped to fit in recesses 39 on spacer 12. As shown in FIG. 4A, each clip 55 includes a protrusion 55a extending toward center line 53 of plate 40, such that clips 55 positioned on the top side 42 of the plate have protrusions 55a extending inferiorly, and clip 55 on the bottom side 44 has a protrusion 55a that extends superiorly. Protrusions 55a are configured to snap into grooves 39a of spacer 12. Protrusions 55a are rectangularly shaped, but in other embodiments clips 55 and protrusions 55a can have any shape that corresponds to the shape of the recesses 39 and grooves 39a. That is, the location and number of clips 55 can be dependent upon the location and number of recesses 39 on spacer, and vice versa. Clips 55 and protrusions 55a can be positioned at any location on plate 40 that is free from intrusion of another feature, i.e. free space, such as for example, lateral sides 46. Further, clips 55 and protrusions 55a of plate 40 snap into the recesses 39 and an interference, friction fit causes secure attachment between spacer 12 and plate 40. In some embodiments, the friction fit is achieved by either slightly oversized or slightly undersized protrusions 55a relative to grooves 39a. Upon attachment of plate 40 to spacer 12, plate 12 is generally flush with spacer 12 so that there is little to no space between plate 40 and spacer 12.

Figure 3:
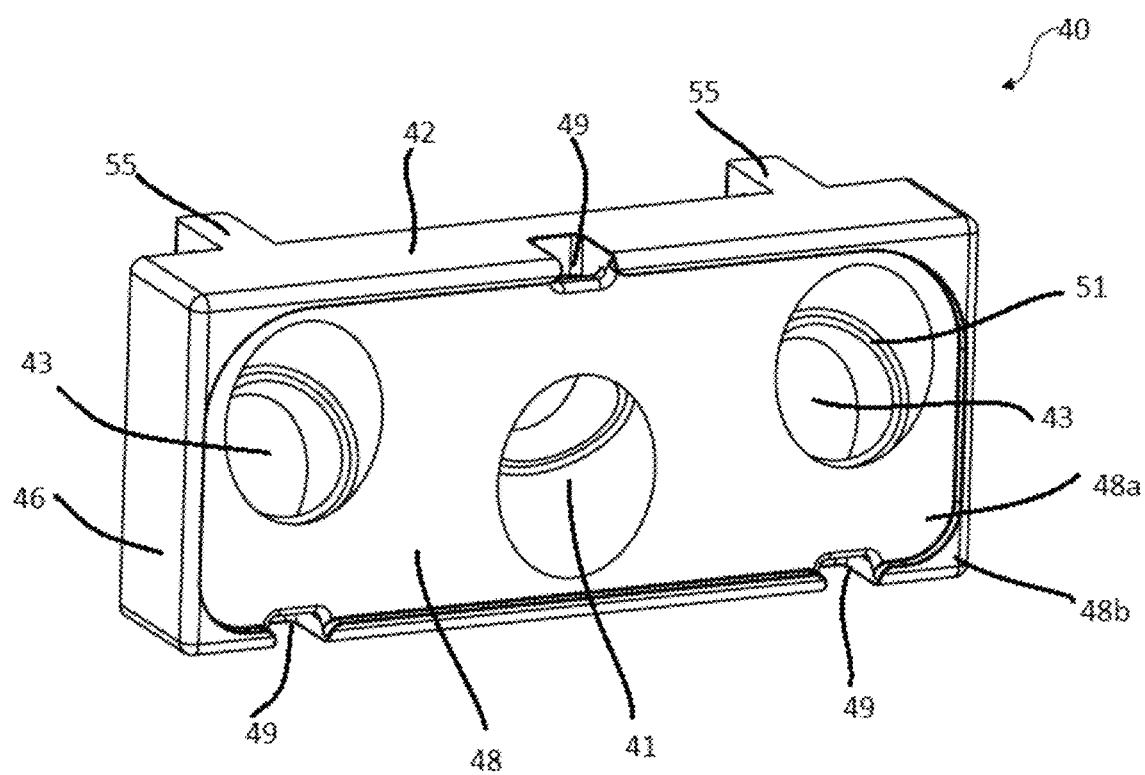
FIG. 3 is a perspective view of a configuration plate which may be attached to spacer 12 of FIG. 1, the configuration plate being in accordance with one embodiment of the present invention.
Figure 4:
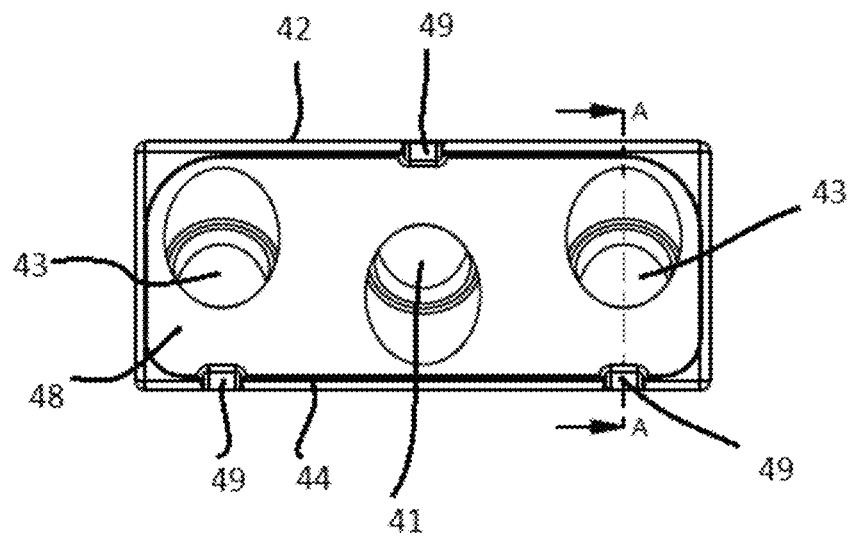
FIG. 4 is an anterior view of the configuration plate of FIG. 3.

As illustrated in FIGS. 3-6, plate 40 includes two holes, or hole extensions, 43 extending from trailing side 48 at a downward angle to leading side 50. Holes 43 are configured to correspond to and align with holes 33 of spacer 12, such that a bone screw can extend through holes 43 and 33 when plate 40 is attached to spacer 12 and engages the bone. The downward angled approach of holes 43 is shown in FIGS. 3 and 4. Plate 40 further includes hole 41 extending from trailing side 48 at an upward angle to leading side 50. This angled approach of hole 41 is illustrated in FIGS. 3-4. In this manner, plate 40 is configured for insertion of angled screws, such as bone screws, to secure prosthesis 10 to superior and inferior vertebrae. In other examples, holes 41, 43 extend through plate 40 at a variety of angles and may have diameters greater or less than those shown. In the present embodiment, holes 41, 43 are not threaded and have an annular shoulder 51 that can abut a head of the screw to limit insertion depth. In other examples holes 31, 33, or alternatively holes 41, 43, may be provided with threads.

Plate 40 further includes a connection feature to connect with retaining mechanism 60, described below. In the illustrated embodiment, the connection feature is recesses 49 and grooves 49a that are substantially similar to recesses 39 and grooves 39a of spacer 12. The shape of the presently shown recesses 49 and grooves 49a can best be seen in FIG. 4A. Recesses 49 of plate 40 are adapted to mate with a corresponding connection feature on retaining mechanism 60, described below. Like recesses 39 of spacer 12, recesses 49 may be any feature known in the art that provides for connection of plate 40 with retaining mechanism 60, and the connection feature is not limited to the recess-clip configuration. Plate 40 has one recess 49 positioned on top side 42 generally superior to hole 41 and two recesses 49 positioned on bottom side 44 generally inferior to holes 43. Trailing side 48 also includes a recessed surface 48a surrounded by a raised surface 48b that acts as a rim. Recessed surface 48a is rectangular in nature with rounded corners and is dimensioned to fit retaining mechanism 60 therein so that an outer surface of retaining mechanism 60 is flush with raised surface 48b when plate 40 and retaining mechanism 60 are assembled together.

Figure 7:
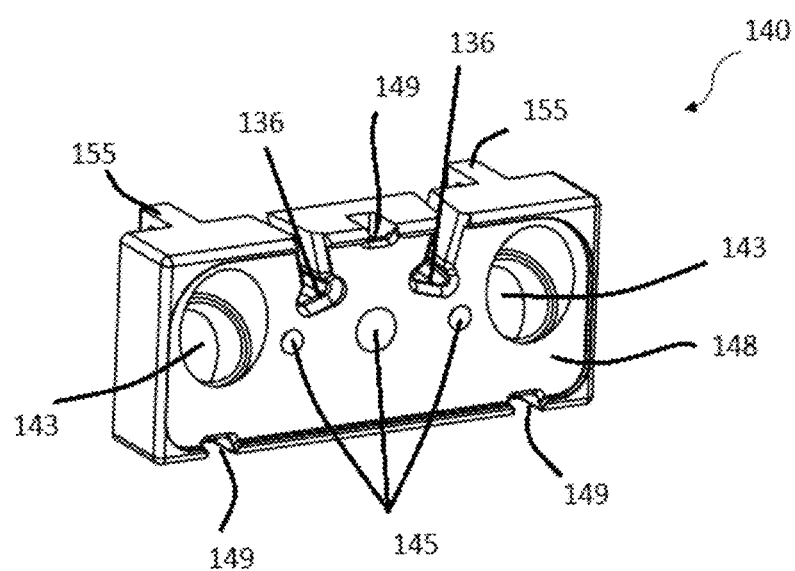
FIG. 7 is a perspective view of a configuration plate which may be attached to spacer 12 of FIG. 1, the configuration plate being in accordance with a second embodiment of the present invention.
Figure 8:
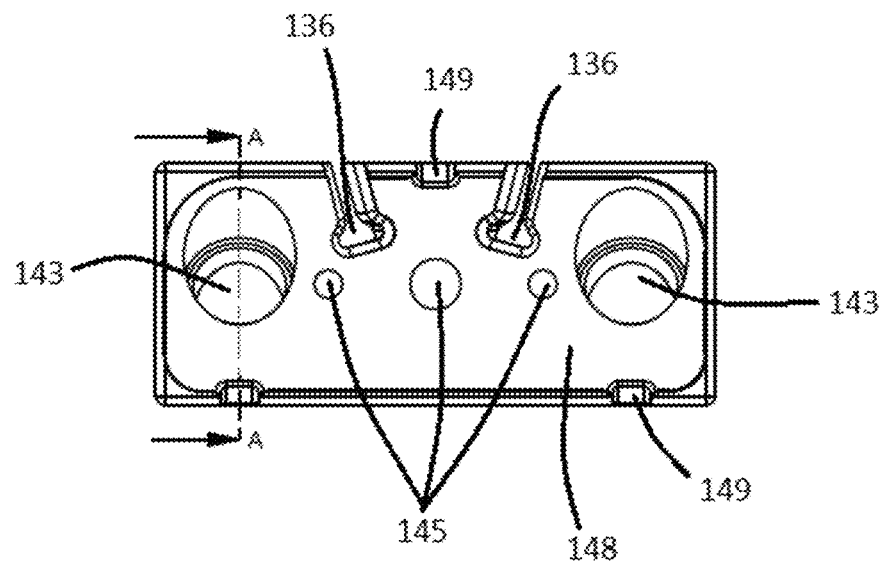
FIG. 8 is an anterior view of the configuration plate of FIG. 7.
Figure 8A:
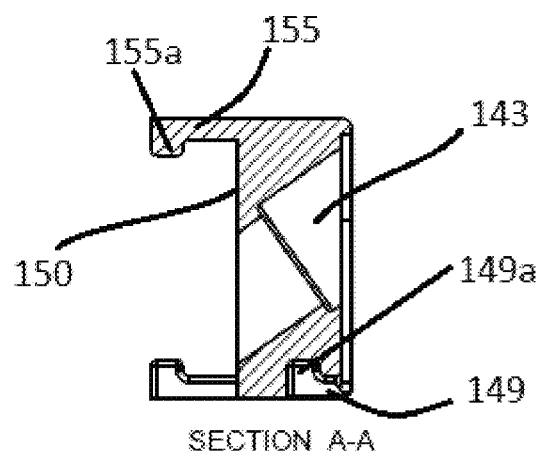
FIG. 8A is a cross section view along section A-A as shown in FIG. 8.

Referring to FIGS. 7-8, another embodiment according to the present invention is a plate 140 that includes hole 143 that are identical to holes 43 of plate 40. Additionally, plate 140 further includes recesses 149 and grooves 149a that are identical to recesses 49 and grooves 49a of plate 40. Clips 155 include protrusions 155a as discussed above. Plate 140 includes two channels or tracks 136 shaped as dovetail slots that extend through plate 140 from trailing side 148 to leading side 150 and inferiorly from top side 42. Channels 136 are configured to correspond to channels 36 of spacer 12, such that an anchor 80, described below, can fit into both channels 36 and 136 and to aid in securing prosthesis 10 to an adjacent vertebra. In this manner, plate 140 is configured to provide fixation with adjacent vertebrae via both anchors and screws. The screws secure prosthesis 10 to the inferior vertebra, and the anchors secure prosthesis 10 to the superior vertebra. Plate 140 also includes a mating feature to mate with instrumentation during insertion of plate 140 and/or prosthesis 10. In the illustrated embodiment, the mating feature is a plurality of holes 145 extending from trailing side 148 to leading side 150 that can be used with one or more instruments during insertion of plate 140 and/or prosthesis 10; however, in other examples, the holes 145 may be positioned and sized differently to accommodate the instrumentation or the mating feature can be any feature that allows for coupling with instrumentation.

Figure 9:
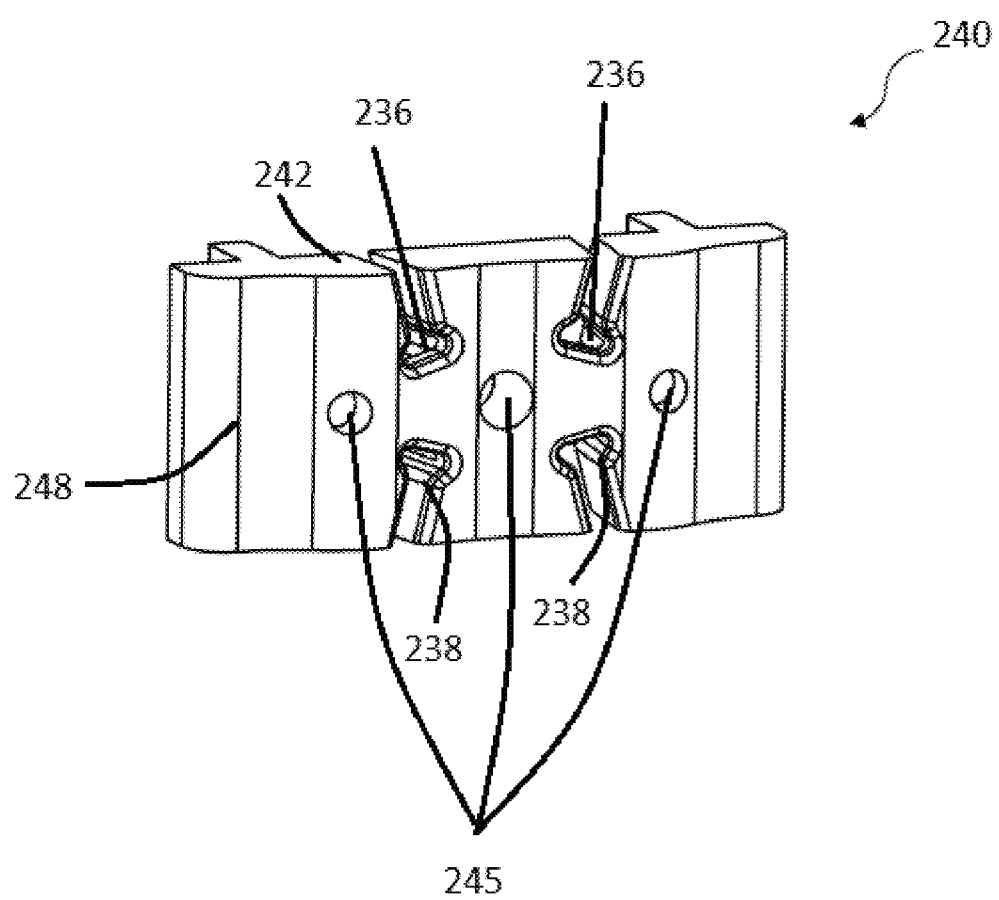
FIG. 9 is a perspective view of a configuration plate which may be attached to spacer 12 of FIG. 1, the configuration plate being in accordance with a third embodiment of the present invention.
Figure 10:
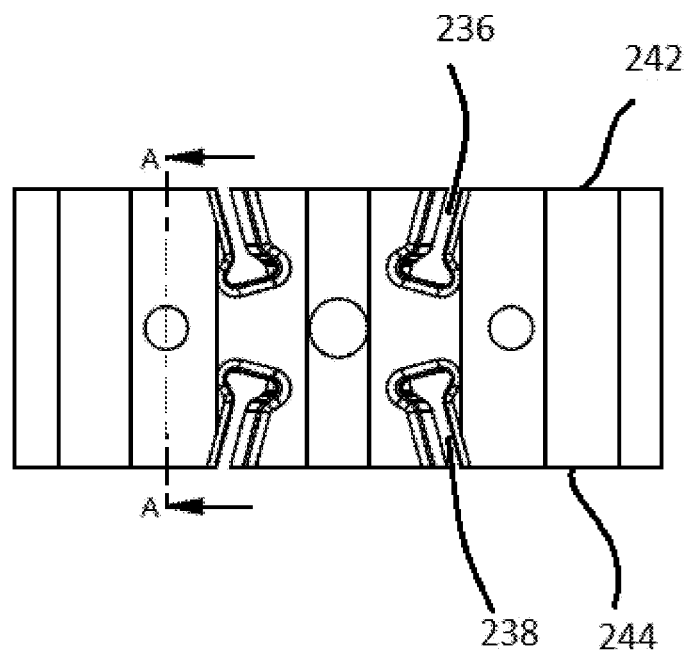
FIG. 10 is an anterior view of the configuration plate of FIG. 9.
Figure 10A:
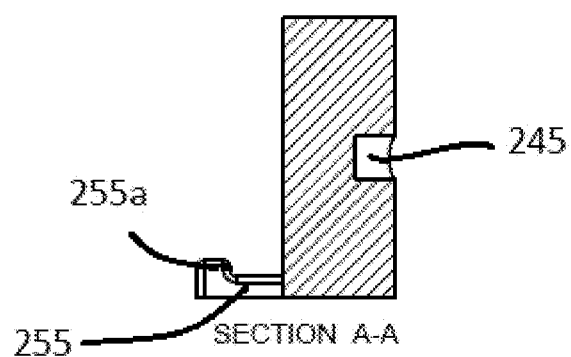
FIG. 10A is a cross section view along section A-A as shown in FIG. 10.
Figure 11:
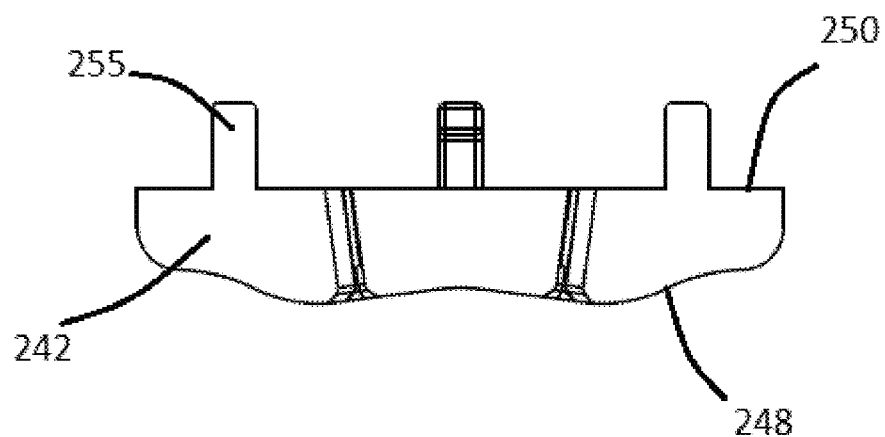
FIG. 11 is a superior view of the configuration plate of FIG. 9.

Referring to FIGS. 9-11, another embodiment according to the present invention is a plate 240 having channels 236 identical to channels 136 of plate 140. Plate 240 further includes channels 238 extending through plate 240 from trailing side 248 to leading side 250 and superiorly from bottom side 244. In this manner, plate 240 is configured to provide fixation with the adjacent vertebrae solely via anchors 80, which can fix into superior and inferior vertebrae, respectively. As shown in FIG. 11, plate 240 includes a curved profile, in a wave-like manner, along trailing side 248. This profile provides stability during attachment of plate 240 to spacer 12. Additionally, the curved profile adds thickness to the implant from trailing side 248 to leading side 250, which corresponds with the length of the interconnection portion 90 of anchor 80, described below. Further, the profile is tapered near lateral sides 46, which reduces the overall footprint of the prosthesis.

Plate 240 may alternatively have a flat profile along trailing side 48 and may include a connection feature, as described above in connection with plates 40, 140, to allow for attachment with retaining mechanism 60.

Figure 12:
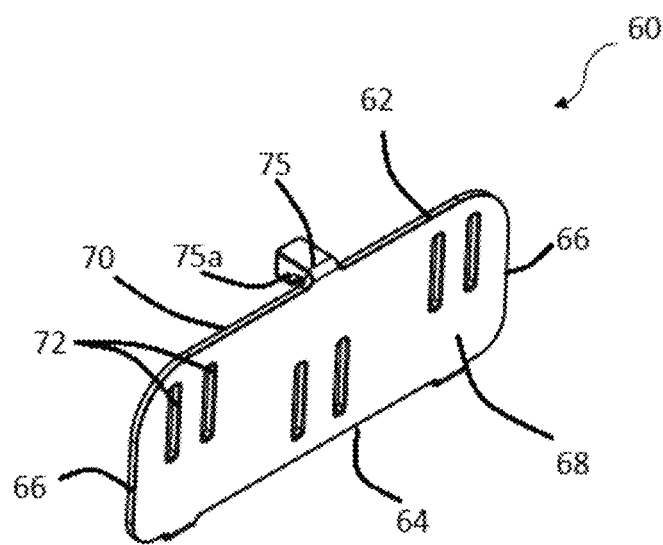
FIG. 12 is a perspective view of a retaining mechanism which may be attached to configuration plates of FIGS. 3 and 7 for use in the prosthesis of one embodiment of the present invention.
Figure 13:
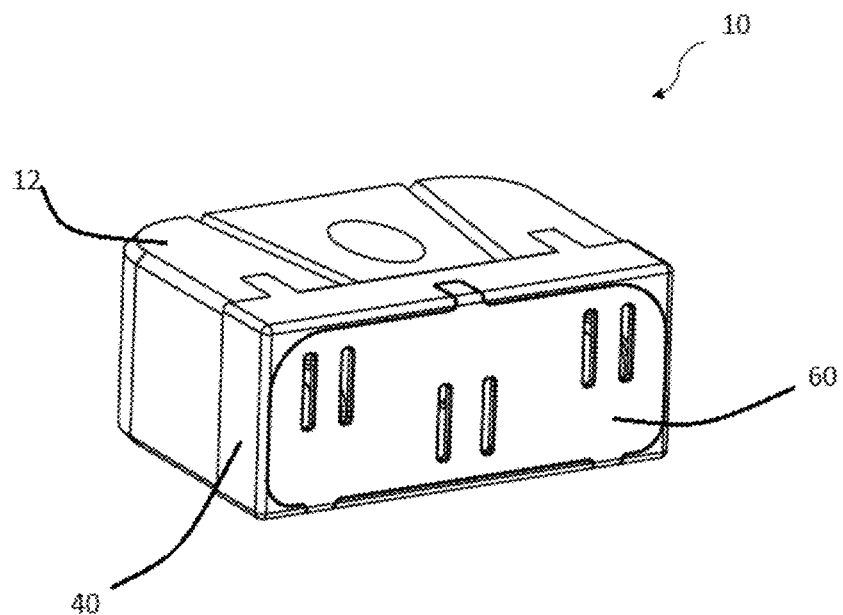
FIG. 13 is a perspective view of a prosthesis having a spacer of FIG. 1, the configuration plate of FIG. 3, and the retaining mechanism of FIG. 12, in accordance with one embodiment of the present invention.

Prosthesis 10 can include a retaining mechanism or plate 60 that is configured to be attached to plate 40 and plate 140. As shown in FIGS. 12 and 13, retaining mechanism 60 is adapted to prevent the bone screws and/or anchors from backing out of the holes in plates 40 and 140, which could cause instability of prosthesis 10 with respect to the vertebrae and discomfort or injury to the patient. As shown in FIG. 12, retaining mechanism 60 includes a top side 62, bottom side 64 opposite the top side, opposing lateral sides 66, trailing side 68, and leading side 70 opposite the trailing side. Retaining mechanism 60 includes a connection feature to correspond with the connection feature of plate 40, 140. In the illustrated embodiment, the connection feature of retaining mechanism 60 is clips 75 and protrusions 75a that are similar in nature to clips 55 and protrusions 55a of plates 40, 140, 240. Clips 75 and protrusions 75a create a friction fit with recesses 49, 149 and grooves 49a, 149a of plates 40, 140 when retaining mechanism 60 is secured thereto, as shown in FIG. 13. However, it is contemplated, as described above, that the connection feature may be any feature known in the art to connect the two bodies. Other locations and numbers of the features are also contemplated.

Retaining mechanism 60 further includes slots 72 extending therethrough from trailing side 68 to leading side 70. Slots 72 are arranged such that they run generally parallel to each other and are positioned anteriorly adjacent to screw holes 41 and 43. However, in other examples, slots 72 may be positioned in different locations and may have the same or different orientation on retaining mechanism 60. Additionally, retaining mechanism may have more or less slots 72, which may be larger or smaller and in a different shape than that shown in FIG. 12. Slots 72 enable a surgeon to visually confirm that screws are properly implanted and also provide ventilation of fluids that may be disposed between retaining mechanism 60 and the corresponding plate 40, 140.

FIG. 13 shows prosthesis 10 according to one embodiment of the present invention, including spacer 12, plate 40, and retaining mechanism 60, each attached via the appropriate clips and recesses. Prosthesis 10 with plate 40 is to be utilized when only bone screw fixation is desirable. While, prosthesis 10 is shown only with configuration plate 40, alternatively, plate 140 could be attached to spacer 12 and retaining mechanism 60.

FIGS. 14-18D show another embodiment of the present invention as a prosthesis 510 that includes a spacer 512 and a retaining mechanism 561 configured to be attached thereto. Spacer 512 includes top and bottom sides 518 and 520, respectively, opposing lateral sides 526, and trailing and leading sides 522 and 524, respectively. Spacer 512 further includes teeth or serrations 528 on each of top and bottom sides 518 and 520, openings 530 for receipt of bone in-growth material, and three holes 533 for receiving fixation members, such as a bone screw. Each hole 533 may include a perimeter at a location about a central axis of the hole that is fully enclosed within the spacer; alternatively, hole 533 may only be partially enclosed within spacer 512. Spacer 512 may further include an opening 546 for engaging with a retaining mechanism 561, shown in FIG. 17, and/or for connection with an inserter instrumentation. Opening 546 is defined by recesses 550, 552 formed in opposing walls 564 and 566 of opening 546. Additionally spacer 512 includes slots 554 adapted to receive a mating feature on retaining mechanism 561 (e.g. projections 555).

Spacer 512 further includes channels 536 and 538 on top side 518 and bottom side 520 of the spacer, respectively. Channels 536 and 538 are shaped similarly to those described above in connection with spacer 12. In the present embodiment, there are two channels on top side 518 and two channels on bottom side 520 of spacer 512. Channels 536, 538 are formed to accommodate anchors 80, described below. In this manner, spacer 512 may be utilized with bone screws and/or anchors to fix spacer 512 to the adjacent vertebrae.

Figure 17:
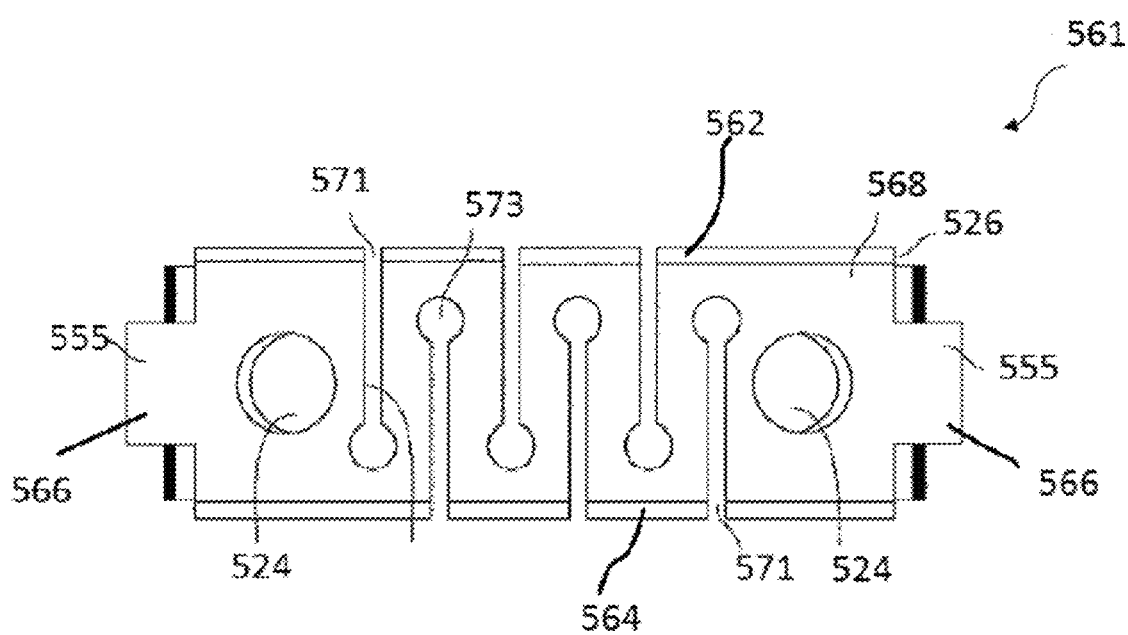
FIG. 17 is an anterior view of a retaining mechanism which may be attached to the spacer of FIG. 14.

Retaining mechanism 561 is configured to be attached to spacer 512 to prevent the bone screws and/or anchors from backing out of the holes and/or channels, respectively. As shown in FIG. 17, retaining mechanism 561 includes a top side 562, a bottom side 564, opposing lateral sides 566, a trailing side 568, and a leading side opposite the trailing side. Retaining mechanism 561 is compressible or otherwise deformable to engage with the spacer 512 and/or to assess fusion if the spacer comprises PEEK. As shown in FIG. 17, retaining mechanism 561 has slots 571 adapted to allow compression or deformation of retaining mechanism 561 upon pressure exerted on lateral sides 566. Slots 571 extend from trailing side 568 to leading side 570 and extend from top side 562 toward bottom side 564 or vice versa while terminating at a circular end 573 in a central portion of retaining mechanism 561. Retaining mechanism 561 may include six slots 571; however, in other examples, there are more or less slots 571 present.

Retaining mechanism 561 includes holes 524 extending from trailing side 564 to leading side 568 that are configured to engage an insertion instrument. This allows such an instrument to exert compression on retaining mechanism to shorten its width when it is installed to spacer 512. Retaining mechanism 561 further includes a connection feature to attach to spacer 512. In the present embodiment, retaining mechanism 561 includes a projection 555 extending from each lateral side 526. Projections 555 are adapted to attach within slots 554 on spacer 512 to provide a secure attachment between the spacer and retaining mechanism 561 when retaining mechanism 561 is in its relaxed or fully extended state. However, other connection features known in the art can be used to attach retaining mechanism to spacer 512, such as for example other types of compression technology. For example, projections 555 can be located at other areas of retaining mechanism 561 to engage spacer 512.

Although described in connection with spacer 512, features similar or identical to retaining mechanism 561 may be used in the retaining mechanism attached with spacer 12.

Figure 14:
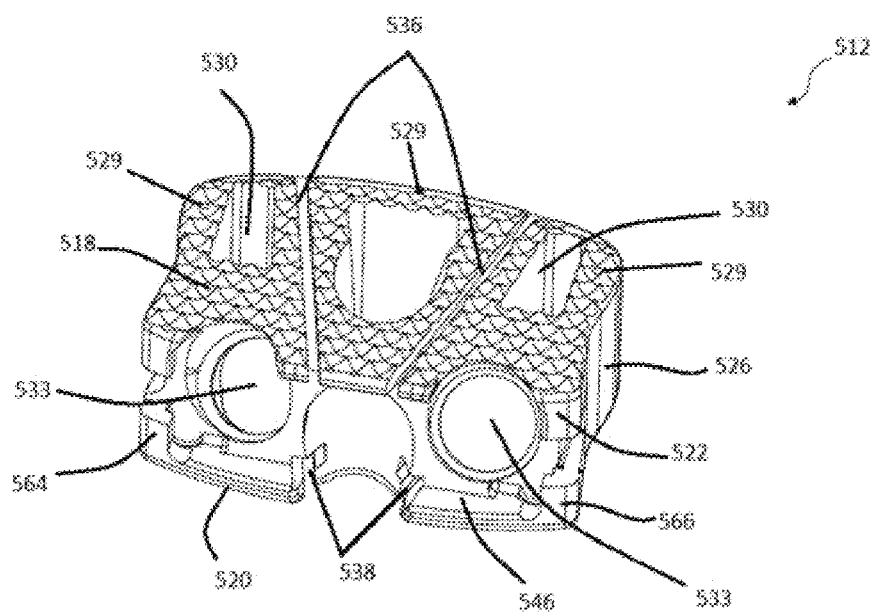
FIG. 14 is a perspective view of a spacer to be used in a prosthesis, in accordance with another embodiment of the present invention.
Figure 15:
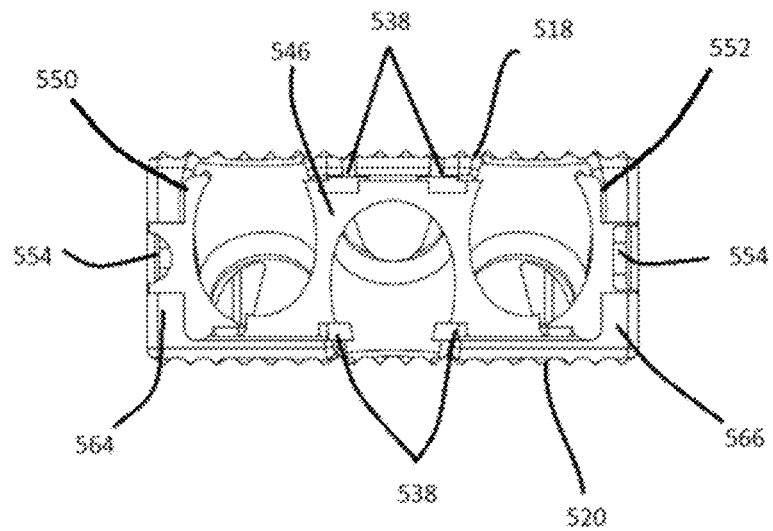
FIG. 15 is an anterior view of the spacer of FIG. 14.
Figure 16:
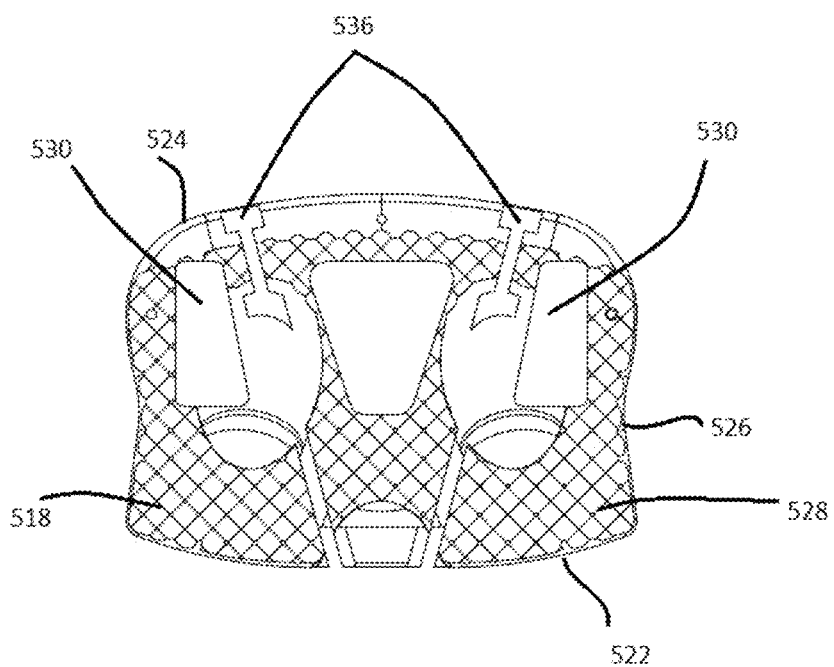
FIG. 16 is a superior view of the spacer in FIG. 14.

Spacers 12 and 512 may include one or more radiographic markers visible in FIGS. 1 and 14 at certain locations 29 and 529 on top sides 18 and 518, respectively. Spacers 12 and 512 can be comprised of radiolucent polyetheretherketone (PEEK), polyaryletherketone (PAEK), or the like. In such cases, radiographic markers allow for visualization of the positioning of spacer 12, 512 in imaging taken during and after a surgical procedure. Alternatively, spacer 12, 512 may comprise metal, for example titanium, ceramic, glass, polymer, or any other material known for use in the human body. Spacer 12, 512 can be comprised of a porous metal or having a porous metal surface such as a porous titanium alloy, including Tritanium® by Howmedica Osteonics Corporation. Spacer 12, 512 may also comprise one or more surface treatments to encourage bony attachment, such as porous coating, plasma spray coating, hydroxyapatite, or tricalcium phosphate. Retaining mechanisms 60 and 561 is preferably comprised of metal, but may be made of PEEK or another composite material.

Certain of the above-described features of spacer 512 and retaining mechanism 561, as well as other aspects of such devices, are further disclosed in U.S. Pat. No. 9,480,577, issued on Nov. 1, 2016, and titled "Retaining Mechanism, Implant, and Tool," the disclosure of which is hereby incorporated by reference herein.

Figure 18A:
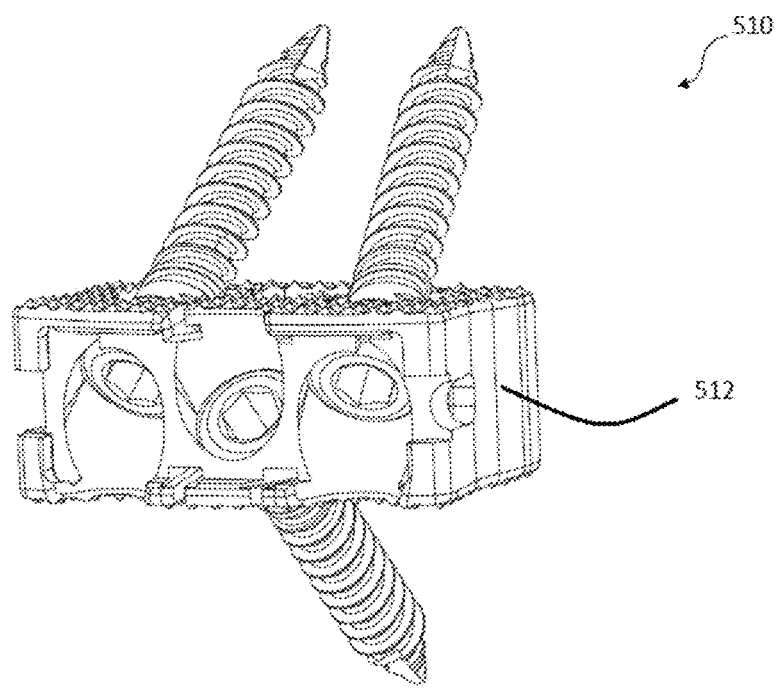
FIGS. 18A-D are various perspective views of the prosthesis with the spacer of FIG. 14 and including in some instances, bone screws or anchors, and including in some instances, the retaining mechanism of FIG. 17.
Figure 18B:
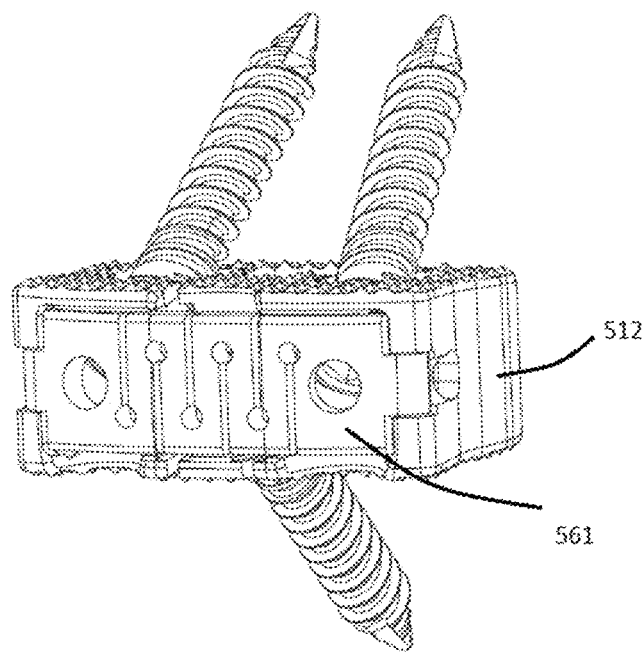
Figure 18C:
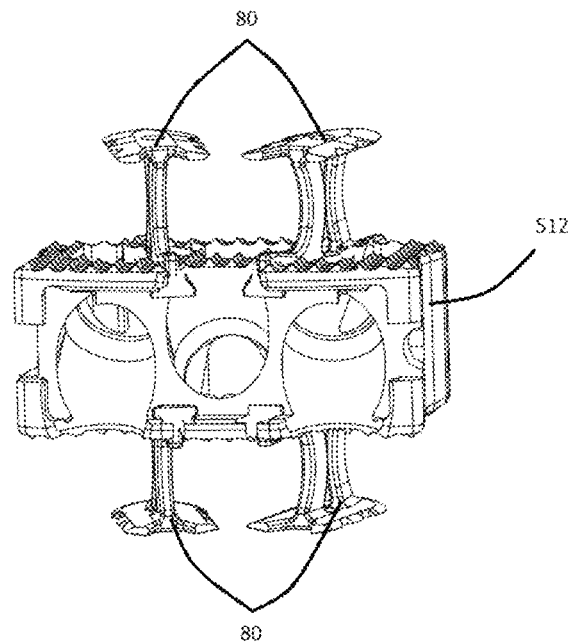
Figure 18D:
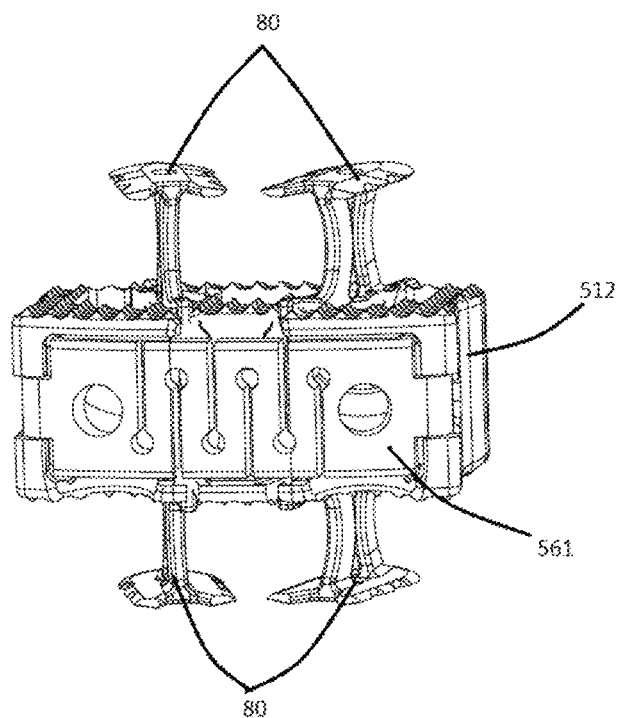

Different configurations of prosthesis 510 are shown in FIGS. 18A-D. FIG. 18A depicts spacer 512 with three bone screws installed therein, and FIG. 18B shows retaining mechanism 561 in place to prevent screw backout. Similarly, FIG. 18C depicts spacer 512 with four anchors 80 installed therein, and FIG. 18D shows retaining mechanism 561 in place to aid in securing anchors 80 and preventing their backout. In other embodiments, any combination of one or more bone screws and one or more anchors 80 can be utilized with spacer 512, with retaining mechanism 561 installed thereafter.

The above-described embodiments are typically sized and shaped for use in the lumbar and thoracic regions of the spinal column. Other sizes, shapes, and geometries of those embodiments are contemplated to adapt them for use in the cervical spine as well.

Figure 19A:
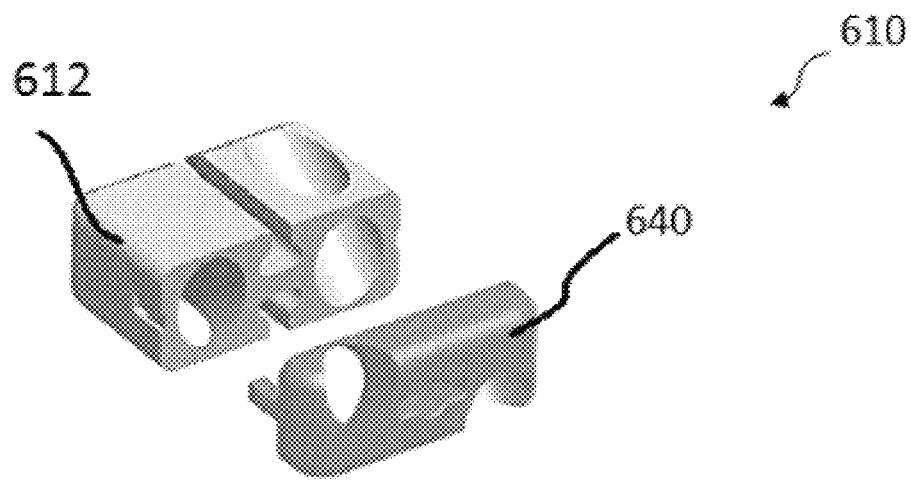
FIGS. 19A-B are perspective views of a prosthesis having a spacer and two embodiments of plates connected thereto for use in cervical surgery.
Figure 19B:
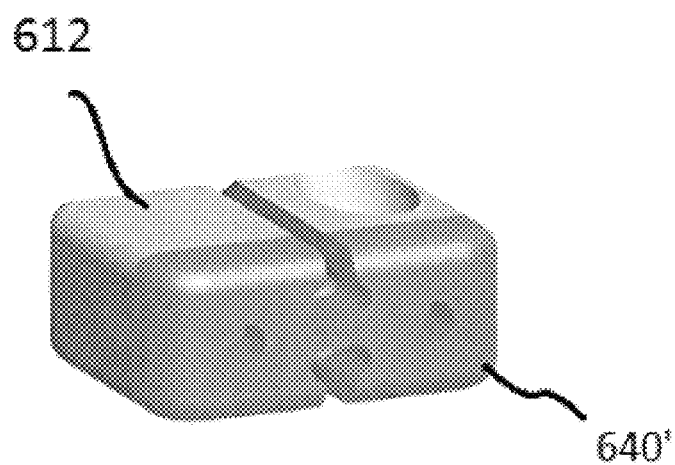

FIGS. 19A and B show spacer 612 and plates 640, 640' that attach to form prosthesis 610 to be used in cervical surgeries. Spacer 612 has similar, but scaled down, features to spacer 12. As shown in FIGS. 19A and B, spacer 612 includes channels or dovetail slots similar to those described in connection with spacer 12. In the illustrated embodiment, the channels are in the shape of a truncated I-beam, but in other examples, the channels may have different shapes, i.e. circular or rectangular, etc. Spacer 612 also includes holes similar to holes 31, 33 of spacer 12. In other examples, the holes of spacer 612 may extend through the spacer at different angles. Further, spacer 612 includes a connection feature to attach plates 640, 640' thereto. In the present embodiment, the connection feature is similar to recesses 39 of spacer 12, however, the recesses of spacer 612 are disposed on the lateral sides. However, spacer 612 may employ any one of, or a combination of, a variety of connection features known in the art. Additionally, spacer 612 may include an opening to allow for receipt of bone in-growth material and may further include serrations on various surfaces, i.e. top and bottom surfaces, to allow for fixation with adjacent vertebrae.

Plates 640, 640' are interchangeable and are both configured to attach to spacer 612. Plate 640 allows for bone screw fixation while plate 640' allows for anchor fixation.

Plate 640 includes a mating hole or hole extension to allow a bone screw to extend through both plate 640 and spacer 612. In the illustrated embodiment, there are two such holes in plate 640; however, there may be more or less of the holes in other examples. The holes may extend through plate 640 at a variety of angles corresponding to alignment with the holes of spacer 612. Plate 640 includes a connection feature to allow for securement of the plate to spacer 612. In the present embodiment, plate 640 includes clips similar to clips 55 on plates 40, 140, 240, that are configured to snap into the recesses of spacer 612; however, in other examples, the connection feature of retaining mechanism 640 may be any known mechanism that secures the two bodies. Additionally, plate 640 includes a mating feature on an anterior surface to allow for engagement with an insertion instrument.

Plate 640' includes a connection feature and a mating feature, similar to those described in connection with plate 640. In the present embodiment, plate 640' includes a plurality of holes similar to holes 145, 245 of plates 140, 240, respectively; although, the mating feature of plate 640' can include any feature known to be used for allowing engagement with such an instrument. Plate 640' further includes channels or channel extensions sized and shaped to align with the channels of spacer 612 and allow for insertion of anchors into prosthesis 610.

Plates 640, 640' may further include a connection feature to connect plate 640, 640' with a retaining mechanism having similar features to those described in connection with retaining mechanisms 60, 561.

Figure 20A:
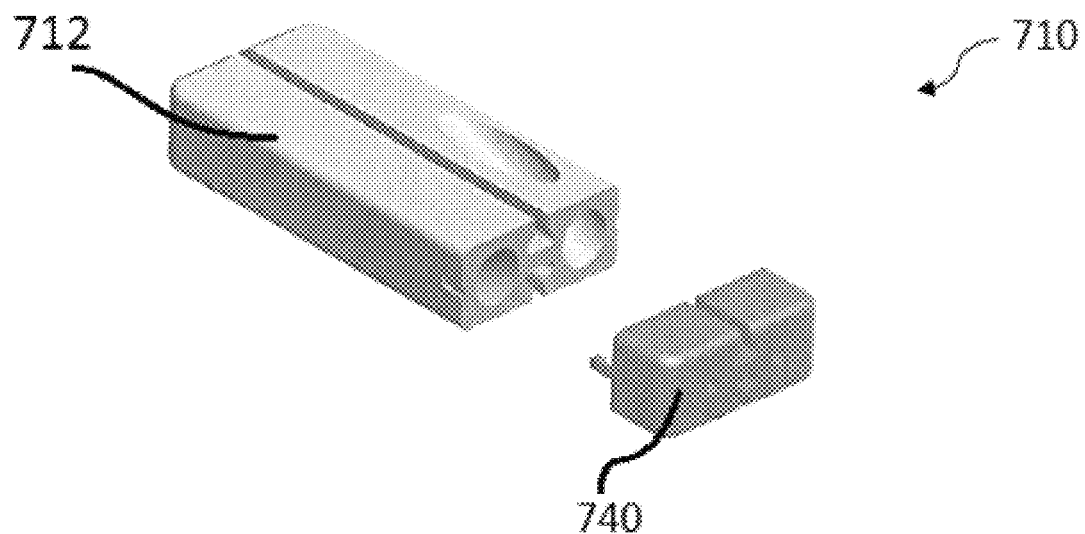
FIGS. 20A-B are perspective views of a prosthesis having a spacer and two embodiments of plates connected thereto for use in lateral lumbar surgery.
Figure 20B:
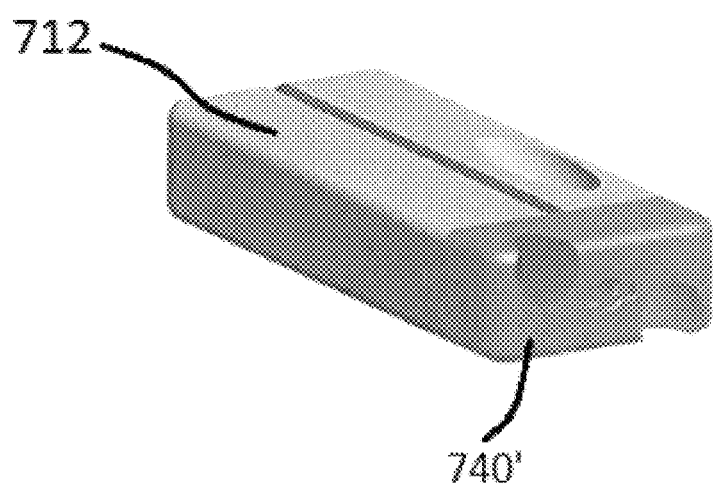

FIGS. 20A and B show prosthesis 710 to be used in lateral surgeries. Prosthesis 710 has spacer 712 with either plate 740 or plate 740' attached thereto. Spacer 712 is similar to spacer 12; however, spacer 712 has dimensions that are greater in the medial-lateral direction and lesser in the anterior-posterior direction as compared to spacer 12. Spacer 712 includes similar features to spacers 12, 612 including: holes for receiving bone screws, channels for receiving anchors, and a connection feature for securement with plates 740, 740'. Additionally, spacer 712 may include serrations and an opening for receipt of bone ingrowth material.

Prosthesis 710 further includes one of plate 740 and 740', which are interchangeable. Plates 740 and 740' both include a connection feature and a mating feature, as described in connection with plates 640, 640'. Plate 740 includes bone screw holes or extensions similar to those described in connection with plates 40, 140, 640. The holes are configured to be aligned with the holes of spacer 712 and to receive bone screws for fixation of prosthesis 710 to bone. Plate 740' includes channels similar to the channels described in connection with plates 140, 240, 640' configured to align with the channels of spacer 712, such that anchors can be inserted into prosthesis 710 and provide fixation of the prosthesis to bone.

Additional plates similar to plates 640, 640', 740, 740' can be utilized to include one or more holes and one or more channels. Specifically, a plate can include one hole and one channel. The features described above can be used in connection with prostheses 610, 710 to be used during cervical and lateral surgeries, respectively. Prostheses 610, 710 include spacers 612, 712 having similar features to spacer 12 and plates 640, 640', 740, 740' having similar features to plates 40, 140, 240. Further prostheses 610, 710 may include a retaining mechanism having similar features to those described in connection with retaining mechanisms 60, 561. Plates 640, 640', 740, 740' may include a connection feature, similar to those described in connection with plates 40, 140, to attach the retaining mechanism to the plate.

Figure 21:
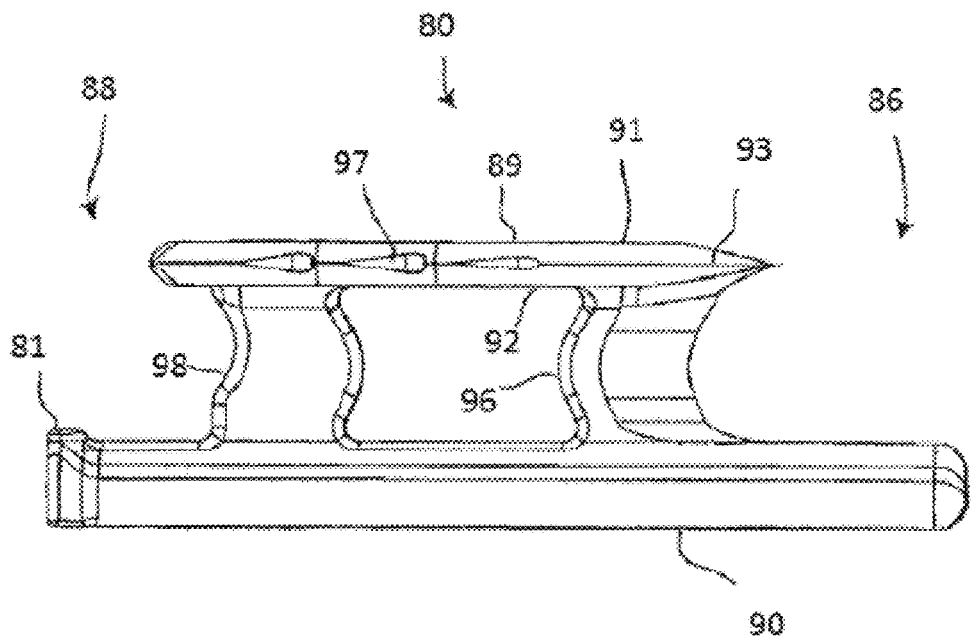
FIGS. 21-23 are perspective views of an anchor to be used with the spacers of FIG. 1 and FIG. 14, in accordance with certain embodiments of the present invention.
Figure 22:
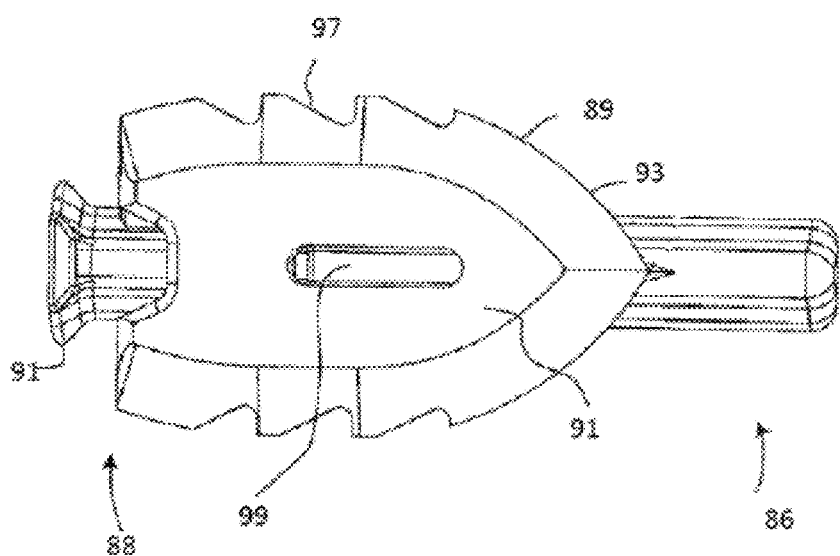
Figure 23:
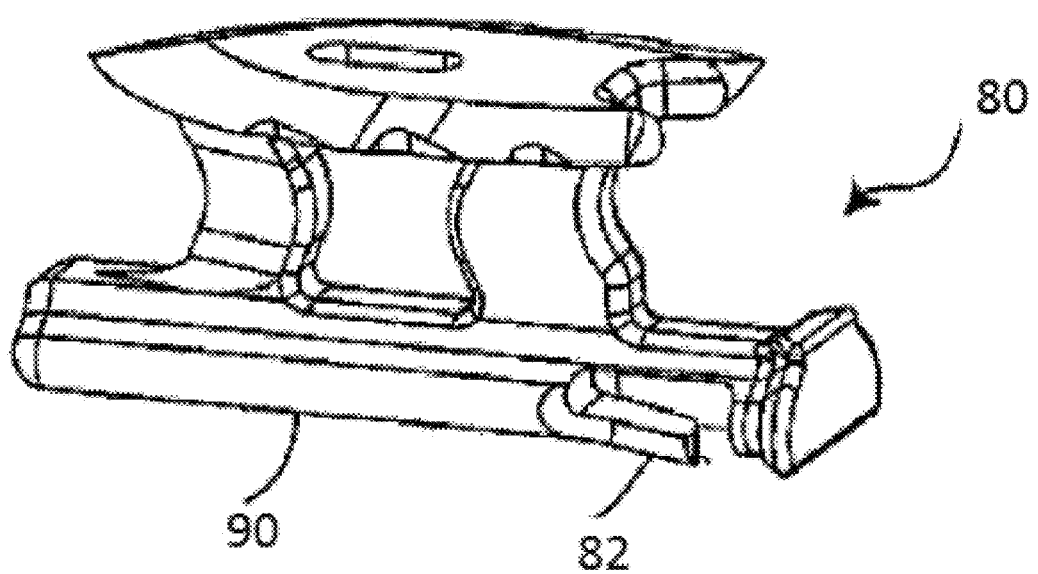

FIGS. 21-23, show anchor 80 used as a fixation method with prosthesis 10 and 510. Anchor 80 may be generally elongate with a leading end 86 and a trailing end 88. The anchor 80 may include an interconnection portion 90 extending between leading end and trailing ends 86, 88. Interconnection portion 90 is shaped and sized to matingly attach with the channels 36, 38 of spacer 12, channels 136 of plate 140, channels 236, 238 of plate 240, and channels 536 and 538 of spacer 512. In the present embodiment, the interconnection portion is a dovetail beam 90 that can slideably attach to the plates and spacers. Anchor 80 includes a stop feature, flange 81, to prevent the anchor from migrating too far posteriorly into prosthesis 10 after implantation. In the illustrated embodiment, the stop feature is flange 81 near trailing end 88. Anchor 80 further includes a locking feature to prevent the anchor from migrating anteriorly after implantation. In the present embodiment, the locking feature is flexible tab 82 disposed near the trailing end 88 of the dovetail beam 90. Flange 81 and flexible tab 82 can cooperate with plates 40, 140, 240 to maintain anchor 80 in its implanted position in the spacer 12.

Anchor 80 includes a fixation portion 89 that secures anchor 80 to the adjacent vertebra. Fixation portion 89 resists axial tensile and compressive forces that may be the result of spinal flexion and extension or right and left lateral bending. In the present embodiment, the fixation portion is a plate 89 extending between the leading and trailing ends 86, 88 and spaced apart from the dovetail beam 90 by leg 96, 98 extending generally perpendicularly between the dovetail beam 90 and fixation plate 89. First leg 96 is positioned near leading end 86, while second leg 98 is positioned near trailing end 88. This positioning of legs 96, 98 allows for an opening between legs 96, 98 so that bone mass may be radiographically viewed. In the present embodiment, plate 89 includes a top surface 91 and a bottom surface 92. Plate 89 tapers to a point at leading end 86, which reduces the magnitude of the force required for insertion of anchor 80 into the bone.

Fixation plate 89 may be sharpened around a portion of its profile to create a cutting edge 93, provided to cut through bone. Cutting edge 93 may extend only on leading end 86 or may extend to the lateral sides of plate 89. In the present embodiment, cutting edge 93 is curved adjacent bottom surface 92 and flat adjacent top surface 91. Cutting edge 93 may additionally be asymmetrically positioned nearer to top surface 91. The curved-flat shape of cutting edge 93 as well as the asymmetric positioning may bias plate 89 and cause it to take a path that may at least slightly diverge from a path taken by dovetail beam 90 as anchor 80 engages prosthesis 10 and one of the adjacent vertebrae. In this manner, anchor 80 lifts away from dovetail beam 90 when inserted. When two or more anchors 80 are placed on superior and inferior sides of prosthesis 10, the adjacent vertebrae are compressed against prosthesis 10 as anchors 80 advance into the bone.

A portion of fixation plate 89 may not be sharpened, specifically a portion near trailing end 88 to prevent the anchor from migrating after implantation. Additionally, cutting edge 93 may include teeth or serrations 97 to further limit migration. Further, plate 89 includes a window 99 extending from top and bottom surfaces of plate 89.

Anchor 80 may be made of metal, ceramic, glass, polymer, or any other structural material known for use in the human body. Anchor 80 may also comprise one or more surface treatments to encourage bony attachment, such as porous coating, plasma spray coating, hydroxyapatite, or tricalcium phosphate. In another example, anchor 80 may comprise autograft bone, allograft bone, or bone graft substitute.

The anchors and other aspects thereof are further disclosed in U.S. Pat. No. 8,349,015, issued on Jan. 8, 2013, and titled "Intervertebral Implant With Integrated Fixation," the disclosure of which is hereby incorporated by reference herein.

A method of implanting intervertebral prosthesis 10 in the lumbar spine from an anterior surgical approach will now be described. It is understood that the same or similar methods may be employed to implant the prosthesis 10 at any level of the spine, and from any surgical approach, including lateral, without departing from the scope of the present invention. More specifically, it is contemplated that prosthesis 10 may be implanted from an anterior, posterior, posterior-lateral, lateral, or other surgical approach.

At least a portion of an intervertebral disc between adjacent vertebrae is removed using tools and techniques known in the art. A surgeon evaluates the bone integrity of the adjacent vertebrae and selects one of plates 40, 140, 240 to be attached to spacer 12. In selecting the plate, the surgeon considers whether screws, anchors, or both are desirable or required for fixation in light of the pathology, patient's anatomy, and/or the surgeon's preference. The selected plate 40, 140, 240 is attached to spacer 12. The spacer-plate configuration is then inserted into the prepared disc space. If the surgeon selects plate 40 or 140, then a screw is inserted into the hole and hole extension of the plates 40, 140 and into communication with the adjacent vertebrae. If the surgeon selects plate 140 or 240, an anchor, such as anchor 80, is inserted into the channel and the channel extension of plates 140, 240 and into communication with the adjacent vertebrae. Of course any number of screws and/or anchors can be used as desirable according to the selected plate. One or more holes and channels can be left empty as well. After the step of inserting the screws and/or anchor into plates 40 or 140, the method can further include the step of attaching retaining mechanism 60 to plate 40 or 140 to prevent screw backout. A tab on anchor 80 interacts with plates 140, 240 to prevent backout.

A method of implanting prosthesis 510 in the lumbar spine from an anterior surgical approach includes inserting spacer 512 into the prepared disc space and inserting a screw and/or anchor, such as anchor 80, into holes 533 and channels 536, 538 and into communication with the adjacent vertebrae. The method further includes attaching retaining mechanism 61 to the spacer 12 by compressing retaining mechanism 61 to prevent backout of the screws and/or anchors.

A method of implanting prosthesis 610 in the cervical spine from an anterior surgical approach includes similar steps to the method of implanting prosthesis 10 in the lumbar spine, as described above. The surgeon evaluates the bone integrity of the adjacent vertebrae, selects the appropriate fixation, screws or anchors, and selects one of plates 640, 640' to be attached to spacer 612. The spacer-plate configuration is then inserted into the prepared disc space. The method of fixation, screws or anchors, are then inserted into the hole, hole extension or channel, channel extension and into communication with the vertebrae. Of course any number of screws and/or anchors can be used as desirable according to the selected plate. One or more holes and channels can be left empty as well.

The methods described in connection with prostheses 10, 610 may be used to implant prosthesis 710 in the lumbar spine but from a lateral surgical approach. Prostheses as described herein can be inserted via an anterior approach, a lateral approach, or a posterior-lateral approach as applicable.

Various surgical instruments can be utilized to insert, position, and even remove the above-described prosthetic devices. For example, certain instruments are further disclosed in U.S. patent application Ser. No. 13/389,298, filed on Jul. 16, 2012, and titled "Intervertebral Implant With Integrated Fixation," U.S. Pat. No. 9,033,993, issued on May 19, 2015, and titled "Intervertebral Implant With Integrated Fixation," and in U.S. Pat. No. 9,480,577, issued on Nov. 1, 2016, and titled "Retaining Mechanism, Implant, and Tool," the disclosures of which are hereby incorporated by reference herein.

Although aspects of the invention(s) herein have been described with reference to particular embodiments, it is to be understood that these embodiments are merely illustrative of certain features of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of using of a kit for intervertebral disc repair, the method comprising:
    selecting one of a first plate or a second plate, wherein the first plate has a hole extension, the second plate has a channel extension, and the first plate is shaped differently from the second plate such that when the first plate is attached to a spacer to form an implant, the hole extension aligns with a hole of the spacer so that a screw may be driven through the hole extension into an anterior end of the hole while the first plate covers an anterior end of a channel of the spacer, whereas when the second plate is attached to the spacer to form the implant, the channel extension aligns with the channel of the spacer so that an anchor may be driven through the channel extension into the anterior end of the channel while the second plate covers the anterior end of the hole of the spacer;
    attaching the selected first plate or second plate to the spacer to form the implant, such that the hole extension aligns with the hole of the spacer while the first plate blocks the anterior end of the channel or the channel extension aligns with the channel of the spacer while the second plate blocks the anterior end of the hole;
    inserting the implant into the disc space; and
    inserting a screw into the hole and the hole extension of the first plate and into communication with an adjacent vertebra or inserting an anchor into the channel and the channel extension of the second plate and into communication with an adjacent vertebra.

2. The method of claim 1, wherein the inserting step is carried out in a lateral approach.

3. The method of claim 1, wherein the channel has a shape different from the hole.

4. The method of claim 1, wherein the method includes inserting the screw into the hole by torquing the screw.

5. The method of claim 1, wherein the method includes inserting the anchor into the channel by sliding the anchor.

6. The method of claim 1, wherein the second plate further includes a hole extension that aligns with the hole of the spacer when the second plate is attached to the spacer.

7. The method of claim 1, further comprising the step of attaching a securing plate to the spacer-plate configuration after the inserting step.

8. The method of claim 7, wherein the securing plate attaches to an anterior surface of the first plate or the second plate.

9. The method of claim 1, wherein the attaching step includes attaching the first plate or the second plate to an anterior surface of the spacer.

10. The method of claim 9, wherein the attaching step includes attaching at least one clip of the first plate or the second plate into a corresponding recess of the spacer.

11. A method for intervertebral disc repair, the method comprising:
    selecting one of a first plate or a second plate for attachment to a spacer;

attaching the selected one of the first plate or the second plate to an anterior surface of a spacer having a hole for receiving a screw and a channel for receiving an anchor, the first plate having a hole extension that aligns with the hole when the first plate is attached to the spacer, and the second plate having a channel extension that aligns with the channel when the second plate is attached to the spacer, wherein a plurality of apertures that includes the hole and the channel is defined in the spacer and the first plate differs in shape from the second plate such that attaching the first plate to the anterior surface of the spacer so that the hole extension aligns with the hole blocks anterior ends of a first subset of apertures within the plurality of apertures whereas attaching the second plate to the anterior surface of the spacer so that the channel extension aligns with the channel blocks anterior ends of a second subset of apertures within the plurality of apertures and the first subset differs from the second subset; and inserting the spacer-plate configuration into a disc space.

12. The method of claim 11, further comprising the step of selecting the first plate or the second plate to be used with the spacer.

13. The method of claim 11, wherein the channel has a shape different from the hole.

14. The method of claim 11, wherein the attaching step includes attaching the first plate and the inserting step includes torquing the screw.

15. The method of claim 11, wherein the attaching step includes attaching the second plate and the inserting step includes sliding the anchor into the channel.

16. The method of claim 11, further comprising the step of inserting a screw into the hole and the hole extension of the first plate and into communication with an adjacent vertebra or inserting an anchor into the channel and the channel extension of the second plate and into communication with an adjacent vertebra.

17. The method of claim 16, further comprising the step of attaching a securing plate to the spacer-plate configuration after the inserting step.

18. The method of claim 11, wherein the attaching step includes attaching at least one clip of the first plate or the second plate into a corresponding recess of the spacer.

19. A method for intervertebral disc repair, the method comprising:

selecting one of a first plate or a second plate for attachment to a spacer;

aligning a hole extension of a first plate with a hole of a spacer or a channel extension of a second plate with a channel of the spacer to create an implant, a perimeter of the hole at a location about a central axis of the hole is fully enclosed within the spacer, wherein the first plate is shaped differently than the second plate so that aligning the hole extension with the hole causes the first plate to prevent driving of an anchor through the channel, whereas aligning the channel extension with the channel does not cause the second plate to prevent driving of the anchor through the channel; and inserting the implant into a disc space.

* * * * *